United States Patent
Petta et al.

(10) Patent No.: US 10,836,711 B2
(45) Date of Patent: Nov. 17, 2020

(54) METHOD FOR THE ONE-POT PRODUCTION OF ORGANO-IODINATED COMPOUNDS

(71) Applicant: GUERBET, Villepinte (FR)

(72) Inventors: Myriam Petta, Montmorency (FR); Stephan Pellinghelli, Bruyeres sur Oise (FR)

(73) Assignee: GUERBET, Villepinte (FR)

( * ) Notice: Subject to any disclaimer, the term of this patent is extended or adjusted under 35 U.S.C. 154(b) by 0 days.

(21) Appl. No.: 16/484,756

(22) PCT Filed: Feb. 9, 2018

(86) PCT No.: PCT/EP2018/053361
§ 371 (c)(1),
(2) Date: Aug. 8, 2019

(87) PCT Pub. No.: WO2018/146285
PCT Pub. Date: Aug. 16, 2018

(65) Prior Publication Data
US 2020/0002269 A1    Jan. 2, 2020

(30) Foreign Application Priority Data
Feb. 10, 2017 (FR) ...................... 17 51121

(51) Int. Cl.
| C07C 231/02 | (2006.01) |
| C07C 231/12 | (2006.01) |
| C07C 235/16 | (2006.01) |
| C07D 319/06 | (2006.01) |

(52) U.S. Cl.
CPC .......... *C07C 231/02* (2013.01); *C07C 231/12* (2013.01); *C07D 319/06* (2013.01); *C07C 235/16* (2013.01)

(58) Field of Classification Search
CPC ... C07C 231/02; C07C 231/12; C07C 235/16; C07D 319/06; C07D 309/06
See application file for complete search history.

(56) References Cited

U.S. PATENT DOCUMENTS

| 3,210,412 A | 10/1965 | Chapman |
| 4,141,894 A * | 2/1979 | Zimmerman ........... C07C 45/62 |
| | | 540/593 |
| 5,670,136 A | 9/1997 | Bacon et al. |

FOREIGN PATENT DOCUMENTS

| EP | 0794937 B1 | 4/1999 |
| EP | 0773925 B1 | 2/2000 |
| GB | 2496971 A | 5/2013 |
| WO | 9616927 A1 | 6/1996 |
| WO | 9637460 A1 | 11/1996 |
| WO | 2006100731 A1 | 9/2006 |
| WO | 2012175903 A1 | 12/2012 |

OTHER PUBLICATIONS

"Constitute, v." OED Online. Oxford University Press, Dec. 2019. Web. Feb. 6, 2020, p. 1.*
March, J., "Advanced Organic Chemistry. Hoboken." (2007): 1-1455 (excerpt p. 425 presented herein).*
Hayashi, "Pot Economy and One-Pot Synthesis", Chemical Science, 2016, pp. 866-880, vol. 7.
Fontanive et al., "Myelography Iodinated Contrast Media. I. Unraveling the Atropisomerism Properties in Solution," Molecular Pharmaceutics, 2015, pp. 1939-1950, vol. 12.

* cited by examiner

*Primary Examiner* — John M Mauro
(74) *Attorney, Agent, or Firm* — Thompson Coburn LLP; Steven M. Ritchey

(57) ABSTRACT

The present invention concerns a process for the preparation of organo-iodized compounds, as well as their preparation intermediates. More particularly, the present invention concerns a process for the preparation of organo-iodized compounds which can be used as preparation intermediates in the synthesis of iodized contrast agents.

10 Claims, No Drawings

METHOD FOR THE ONE-POT PRODUCTION OF ORGANO-IODINATED COMPOUNDS

CROSS-REFERENCE TO RELATED APPLICATIONS

This application is a U.S. National Phase application of PCT/EP2018/053361 filed on Feb. 9, 2018, claiming the benefit of French Application No. 1751121, filed on Feb. 10, 2017, both of which are incorporated herein by reference in their entireties.

The present invention relates to a process for the preparation of organo-iodized compounds, as well as their preparation intermediates. More precisely, the present invention relates to a process for the preparation of organo-iodized compounds used as preparation intermediates in the synthesis of iodized contrast agents.

Currently, the majority of processes for the synthesis of iodized contrast agents use the dichloride of 5-amino-2,4,6-triiodoisophthalic acid (also known as DiCOCl), with the following formula:

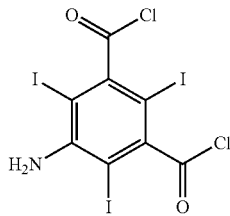 [SMILES: Nc1c(I)c(C(=O)Cl)c(I)c(C(=O)Cl)c1I]

This compound is used in particular as an intermediate product in the synthesis of many contrast agents such as iopamidol (Iopamiron®), iohexol (Omnipaque®), ioversol (Optiray®), iomeprol (Iomeron®) or iobitridol (Xenetix®).

During the synthesis of iodized contrast agents, it is necessary to carry out lengthy steps for separation and purification in order to obtain synthesis intermediates with a good level of purity. These steps considerably increase the time for carrying out the synthesis, and thus increase the costs involved in employing those methods for the preparation of contrast agents.

One of the steps in the production of DiCOCl is a step for the chlorination (also known as chloride formation) of 5-amino-2,4,6-triiodoisophthalic acid (AATI) with a chlorination agent such as thionyl chloride, also known as thionyl dichloride ($SOCl_2$). This chlorination is a slow step (more than 7 hours 30 minutes reaction time) and is energy-consuming because it is carried out at a high temperature of more than 48° C. A large excess of chlorination agent with respect to the AATI means that the kinetics are faster, but using such an excess is not acceptable from an industrial and environmental viewpoint. In fact, in contact with water, thionyl chloride releases hydrogen chloride (HCl) and sulfur dioxide ($SO_2$), which are corrosive and irritant gases. The use of catalysts for this chlorination reaction has been recommended in order to be able to reduce the quantity of $SOCl_2$ used while obtaining a good industrial yield.

The processes used for the preparation of DiCOCl also suffer from the disadvantage of generating a large quantity of effluents because large quantities of water are used at the time of the "precipitating" hydrolysis of the DiCOCl obtained from the chlorination step. As an example, in the application EP 0 794 937, the addition of 22.2 to 33 equivalents of water per equivalent of AATI is described (Examples 1 to 3), or in EP 0 773 925, the addition of 120 equivalents of water is described for the hydrolysis of thionyl chloride (see Example 1-E). Finally, these processes necessitate carrying out purification steps by precipitation, filtration and drying, in order to ensure that the reactivity is optimal and the yield is competitive in the subsequent steps. It should also be noted that the drying step may prove to be dangerous because it runs an industrial risk of exothermic degradation, and thus has to be carried out under highly controlled and restrictive conditions.

Following this chlorination step, the DiCOCl is acylated. This step is very lengthy because it can last several tens of hours (sometimes up to 70 hours). It also involves purification steps and steps for isolation by draining and drying in order to obtain an intermediate in the synthesis of iodized contrast agents. The drying step presents the risk highlighted above. In addition, this step involves the use of large excesses of certain reagents which can prove to be costly in some cases, both in terms of purchasing them and also in terms of their synthesis. Handling of certain of these reagents (for example DiCOCl) can also pose problems because of their granulometry. For this acylation step alone, yields are obtained which are limited to approximately 87.5%. The yield for the chlorination step is approximately 90.5%. The yield for the combination of the chlorination and acylation steps is thus approximately 79.2%.

Preparation processes involving an acylation followed by a chlorination which also suffer from the same disadvantages as those mentioned above are also known.

In particular, the application WO 2012/175903 describes obtaining an acylated AATI obtained using a large excess of acylation agent. This acylated intermediate compound is then isolated, filtered and dried before being chlorinated.

As a consequence, there is a need for an improved process for the preparation of iodized contrast agents. More particularly, there is a need for a process for the preparation of iodized contrast agents which is applicable on an industrial scale, and which is cheaper, rapid and safe.

The aim of the present invention is to provide a process for the preparation of organo-iodized products, and more particularly of synthesis intermediates for iodized contrast agents, which can overcome the disadvantages mentioned above.

The aim of the present invention is also to provide a process for the preparation of organo-iodized compounds which is applicable on an industrial scale, in particular a safe, rapid and economical process which is acceptable from an environmental viewpoint.

The aim of the present invention is to provide a process for the preparation of organo-iodized compounds in a good yield, and in particular a better yield compared with known processes.

Thus, the present invention concerns a process for the preparation of an organo-iodized compound, comprising the following steps:
   a) acylation of 2,4,6-triiodo-5-aminoisophthalic acid with the following formula (A):

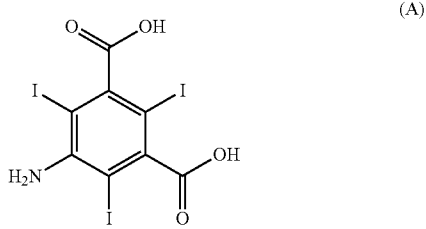

(A)

in order to obtain an intermediate compound Y; then
   b) chlorination of the intermediate compound Y obtained in step a);
   the steps a) and b) being carried out without isolation of the intermediate compound Y.

Surprisingly, the inventors have developed a one-pot process which can be used to carry out the steps a) for acylation and b) for chlorination in the same reaction medium and without the need for isolation of the acylated reaction intermediates obtained in step a) (intermediate compounds Y). Thus, acylation of the AATI is carried out, then is directly followed by chlorination of said acylated AATI, thereby resulting in an organo-iodized compound of interest with a satisfactory level of purity and without isolation of the acylated AATI.

The succession of steps a) for acylation and b) for chlorination in accordance with the invention thus corresponds to a one-pot concatenation.

The preparation process in accordance with the invention can advantageously be used to avoid the steps for separation and purification of intermediate synthesis compounds Y: precipitation or washing solvents are avoided, as well as treatment of the corresponding mother liquors. The preparation process in accordance with the invention is thus more economic, more rapid and more environmentally friendly.

The process in accordance with the invention can be applied on an industrial scale and can in particular be used to obtain cumulative yields of at least 80% for the one-pot concatenation of steps a) and b).

The preparation process in accordance with the invention also has the advantage of generating soluble intermediates (the term "soluble" means that the process does not generate crystals).

Definitions

The process in accordance with the invention comprises a one-pot concatenation of steps a) and b), in which the intermediate compound Y obtained from the acylation (step a)) is not isolated before proceeding to the chlorination (step b)).

A preparation process or a concatenation of one-pot reactions is a process/concatenation in which a synthesis intermediate, for example AATI, undergoes several successive and/or simultaneous reactions in its reaction medium, avoiding the steps of separation and purification of the intermediate compounds (for example the intermediate compounds Y).

The term "organo-iodized" compound means an organic compound comprising at least one carbon atom and at least one iodine atom, for example 1, 2, 3, 4 or 5 iodine atoms, preferably 3. Said organic compound optionally comprises one or more atoms of hydrogen, oxygen, nitrogen, sulfur, phosphorus, halogen or a combination of these atoms. Preferably, the organo-iodized compound comprises one or more atoms of hydrogen (hydrocarbon compound), oxygen, nitrogen and optionally chlorine.

The term "acylation" means a chemical reaction during which an acyl group is added to an organic compound such as AATI by the action of an acylation agent.

The term "chlorination", also known as chloride formation, means the substitution of an atom and/or a group of atoms of an organic compound with a chlorine atom, preferably the substitution of a hydroxyl group (—OH) with a chlorine atom (—Cl), by the action of a chlorination agent or chlorinator, more preferably the double substitution of the hydroxyl groups (—OH) present on two carboxylic acid functions with a chlorine atom (—Cl).

In accordance with the present invention, the expression "reaction medium" designates the medium in which the steps a) for acylation and b) for chlorination in accordance with the invention take place. In accordance with one embodiment, said reaction medium comprises at least one solvent and at least one reagent such as AATI and/or an acylation agent and/or a chlorination agent.

The term "isolation" denotes the separation of an organo-iodized compound, preferably the intermediate compound Y, from the reaction medium in accordance with the invention, optionally followed by its purification. Methods for the separation and/or purification of an organo-iodized compound are known to the person skilled in the art. Filtration, chromatography (which may or may not be on grafted silica, for example), centrifuging, solvent extraction, crystallization, adsorption (for example onto charcoal) and distillation may be cited by way of example.

The term "$(C_1$-$C_{20})$alkyl" means a saturated hydrocarbon group containing 1 to 20 carbon atoms, which may be linear or branched. The term "branched" means that one or more alkyl group(s) are attached to a linear alkyl. Preferably, the alkyls are selected from methyl, ethyl, propyl and isopropyl.

The term "$(C_1$-$C_{20})$alkenyl" means alkyls as defined above and comprising one or more double carbon-carbon bond(s) (ethylenically unsaturated). When they comprise a single double bond, they may typically be represented by the formula $C_nH_{2n}$, where n represents the number of carbon atoms. Particular alkenyl radicals which may be cited are allyl or vinyl radicals.

The term "$(C_1$-$C_{20})$alkynyl" means alkyls as defined above and comprising one or more triple carbon-carbon bond(s) (acetylenically unsaturated). When they comprise a single triple bond, they may typically be represented by the formula $C_nH_{2n-2}$, where n represents the number of carbon atoms. Particular alkynyl radicals which may be cited are acetylene, and the ethynyl or propynyl groups.

The term "$(C_3$-$C_{10})$cycloalkyl" means a saturated and cyclic hydrocarbon group, for example monocyclic or bicyclic, containing 3 to 10 carbon atoms. Cycloalkyls which may be cited include cyclopropyl, cyclopentyl or cyclohexyl.

The term "$(C_6$-$C_{10})$aryl" means a cyclic aromatic group (monocyclic, bicyclic or tricyclic) containing 6 to 10 carbon atoms, for example phenyl and naphthyl. Preferably, the aryl group is a phenyl.

The term "heterocyclyl containing 3 to 10 atoms" means a cycloalkyl as defined above and in which 1 or more carbon atoms have been replaced by one or more heteroatoms such as oxygen, sulfur or nitrogen. As an example, the heterocyclyls comprise 1 or 2 atom(s) of nitrogen, 1 or 2 atom(s) of oxygen, 1 or 2 atom(s) of sulfur or a combination thereof. Particular heterocyclyls which may be cited include epoxyethyl, oxiranyl, aziridinyl, tetrahydrofuranyl, dioxolanyl, pyrrolidinyl, pyrazolidinyl, imidazolidinyl, tetrahydrothiophenyl, dithiolanyl, thiazolidinyl, tetrahydropyranyl, dioxanyl, morpholinyl, piperidyl, piperazinyl, tetrahydrothiopyranyl, dithianyl, thiomorpholinyl, dihydrofuranyl, 2-imidazolinyl, 2,-3-pyrrolinyl, pyrazolinyl, dihydrothiophenyl, dihydropyranyl, pyranyl, tetrahydropyridyl, dihydropyridyl, tetrahydropyrinidinyl, dihydrothiopyranyl, and the corresponding groups obtained from fusion with a phenyl ring, and more particularly the cycles morpholinyl, dioxalanyl, benzothiazolidinyl, pyrrolidinyl and benzopyrrolidinyl. Preferably, the heterocyclyl is a dioxanyl.

The term "heteroaryl comprising 6 to 10 atoms" means an aryl as defined above and in which 1 or more carbon atoms have been replaced by one or more heteroatoms such as oxygen, sulfur or nitrogen. As an example, the heteroaryls comprise 1 or 2 atom(s) of nitrogen, 1 or 2 atom(s) of oxygen, 1 or 2 atom(s) of sulfur or a combination thereof. Heteroaryl radicals which may be cited include pyrazinyl, thienyl, oxazolyl, furazanyl, pyrrolyl, 1,2,4-thiadiazolyl, naphthyridinyl, pyridazinyl, quinoxalinyl, phthalazinyl, imidazo[1,2-a]pyridine, imidazo[2,1-b]thiazolyl, cinnolinyl, triazinyl, benzofurazanyl, azaindolyl, benzimidazolyl, benzothienyl, thienopyridyl, thienopyrimidinyl, pyrrolopyridyl, imidazopyridyl, benzoazaindole, 1,2,4-triazinyl, benzothiazolyl, furanyl, imidazolyl, indolyl, triazolyl, tetrazolyl, indolizinyl, isoxazolyl, isoquinolinyl, isothiazolyl, oxadiazolyl, pyridazinyl, pyrazolyl, pyridyl, pyrimidinyl, purinyl, quinazolinyl, quinolinyl, isoquinolyl, 1,3,4-thiadiazolyl, thiazolyl, carbazolyl, as well as the corresponding groups obtained from their fusion or from fusion with the phenyl ring.

The term "halogen" refers to the atoms from group 17 of the periodic table of the elements, and in particular includes fluorine, chlorine, bromine and iodine atoms. Preferably, the halogen is a chlorine atom.

The present invention also encompasses stereoisomers, hydrates, solvates, organic or mineral salts of the organo-iodized compounds, preferably with general formula (I), and intermediate compounds Y. Their tautomeric, enantiomeric, atropisomeric, diastereoisomeric and epimeric forms are also encompassed.

Process for the Preparation of an Organo-Iodized Compound

In accordance with one embodiment, the steps a) for acylation and b) for chlorination of the process in accordance with the invention are carried out without isolation of the intermediate compound Y in a single reactor or in several reactors, preferably in a single reactor.

In accordance with one embodiment, the acylation of 2,4,6-triiodo-5-aminoisophthalic acid with the following formula (A):

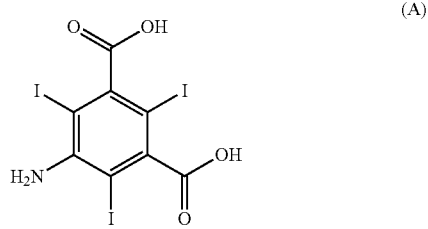 [SMILES: Nc1c(I)c(C(=O)O)c(I)c(C(=O)O)c1I]

is carried out using an acyl chloride.

In accordance with one particular embodiment, the process in accordance with the invention comprises the following steps:
a) acylation of 2,4,6-triiodo-5-aminoisophthalic acid with the following formula (A):

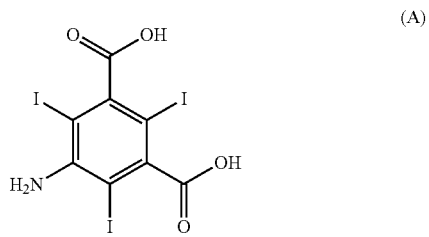 [SMILES: Nc1c(I)c(C(=O)O)c(I)c(C(=O)O)c1I]

by a compound with the following general formula (II):

in order to obtain an intermediate compound Y; then
b) chlorination of the intermediate compound Y in order to obtain an organo-iodized compound with the following general formula (I):

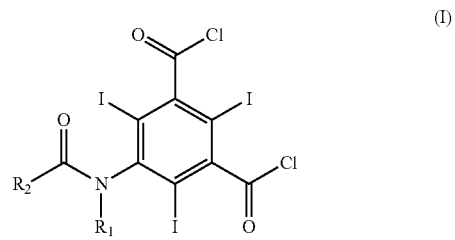

$R_1$ being H or a methyl group, $R_1$ preferably being H, and
$R_2$ being selected from the group constituted by:
($C_1$-$C_{20}$)alkyl, linear or branched;
($C_1$-$C_{20}$)alkenyl, linear or branched;
($C_1$-$C_{20}$)alkynyl, linear or branched;
($C_3$-$C_{10}$)cycloalkyl;
($C_6$-$C_{10}$)aryl;
a heterocyclyl comprising 3 to 10 atoms; and
a heteroaryl comprising 6 to 10 atoms;
said alkyl, alkenyl and/or alkynyl groups optionally being substituted with one or more substituent(s) selected from the group constituted by atoms of halogen, oxygen and nitrogen;
said alkyl, alkenyl and/or alkynyl groups optionally being interrupted by one or more group(s) selected from the group constituted by —O—, —C(O)—O— and —O—C(O)—; and
said cycloalkyl, heterocyclyl, aryl and/or heteroaryl groups optionally being substituted with one or more substituent(s) selected from the group constituted by ($C_1$-$C_{20}$)alkyl, which may be linear or branched, and atoms of halogen, oxygen and nitrogen.

In accordance with one embodiment, in order to obtain compounds with formula (I) mentioned above in which $R_1$ is a methyl group, the process of the invention comprises a supplemental step for acylation of 2,4,6-triiodo-5-aminoisophthalic acid by a compound with formula Me-C(O)Cl.

In accordance with another embodiment, in order to obtain compounds with formula (I) mentioned above in which $R_1$ is a methyl group, the process of the invention comprises a supplemental step for acylation of the intermediate compound Y by a compound with formula Me-C(O)Cl.

As indicated above, when $R_2$ is an alkyl, alkenyl or alkynyl group, this may be substituted with at least one nitrogen atom; as an example, the alkyl, alkenyl or alkynyl groups may be substituted with at least one amine function (primary, secondary or tertiary), or may be interrupted by a —NH— or —N(($C_1$-$C_6$)alkyl) group, or indeed, when $R_2$ is an alkynyl group, may be interrupted by at least one nitrogen atom.

In accordance with one embodiment, $R_2$ is selected from the group constituted by:

($C_1$-$C_{10}$)alkyl, linear or branched;

($C_1$-$C_{10}$)alkenyl, linear or branched;

($C_1$-$C_{10}$)alkynyl, linear or branched;

($C_3$-$C_{10}$)cycloalkyl;

a heterocyclyl comprising 3 to 10 atoms; and said alkyl, alkenyl and/or alkynyl groups optionally being substituted with one or more substituent(s) selected from the group constituted by halogen atoms;

said alkyl, alkenyl and/or alkynyl groups optionally being interrupted by one or more group(s) selected from the group constituted by —O—, —C(O)—O— and —O—C(O)—; and said cycloalkyl and/or heterocyclyl groups optionally being substituted with one or more substituent(s) selected from the group constituted by ($C_1$-$C_{10}$)alkyl, which may be linear or branched, and halogen atoms.

Preferably, $R_2$ is selected from the group constituted by:

($C_1$-$C_{20}$)alkyl, linear or branched; and a heterocyclyl comprising 3 to 10 atoms;

said alkyl group optionally being substituted with one or more substituent(s) selected from the group constituted by halogen atoms;

said alkyl group optionally being interrupted by one or more group(s) selected from the group constituted by —O—, —C(O)—O or —O—C(O)—; and said heterocyclyl group optionally being substituted with one or more substituent(s) selected from the group constituted by ($C_1$-$C_{20}$)alkyl, which may be linear or branched, and halogen atoms.

More particularly, $R_2$ is selected from the group constituted by:

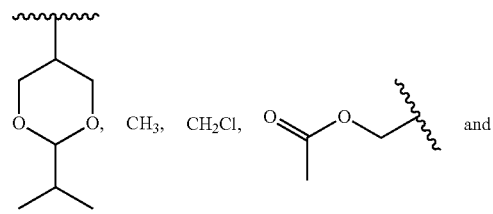

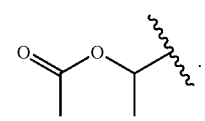 [SMILES: *C(C)OC(C)=O]

When mention is made of the group

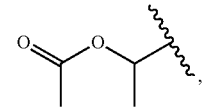

then this includes mention of both its (R) isomer and its (S) isomer, or in fact a racemic mixture of the (R) and (S) isomeric forms of this group.

In accordance with one particular embodiment, $R_2$ is selected from the group constituted by:

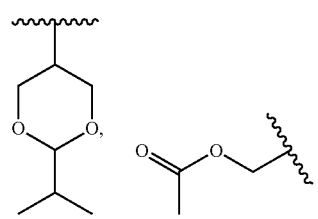

and $CH_2Cl$; preferably, $R_2$ is:

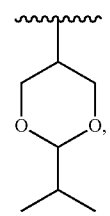

In particular, the organo-iodized compounds obtained, preferably the organo-iodized compounds with general formula (I), are those below and can be used in the preparation of the corresponding contrast agents indicated in Table 1 below.

TABLE 1

Organo-iodized compounds with general formula (I) and corresponding contrast agents

| Chemical formula of organo-iodized compound with general formula (I) | Name of organo-iodized compound with general formula (I) | Name of contrast agent for which it is the synthesis intermediate |
|---|---|---|
| (structure) | 5-[[[2-(1-methylethyl)-1,3-dioxan-5-yl]carbonyl]amino]-2,4,6-triiodo-1,3-benzenedicarbonyl dichloride (or DICOA) | Iobitridol |
| (structure) | 5-{[(2S)-2-(acetyloxy)-1-oxopropyl]amino-2,4,6-triiodo-1,3-benzene dicarbonyl dichloride | Iopamidol |
| (structure) | 5-(acetylamino)-2,4,6-triiodobenzene-1,3-dicarbonyl dichloride | Iohexol Iodixanol |
| (structure) | 5{[(acetyloxy)acetyl]amino}-2,4,6-triiodobenzene-1,3-dicarbonyl dichloride | Ioversol |
| (structure) | 5-[(chloroacetyl)amino]-2,4,6-triiodobenzene-1,3-dicarbonyl dichloride | Ioversol |
| (structure) | 5-{[(acetyloxy)acetyl]methylamino}-2,4,6-triiodobenzene-1,3-dicarbonyl dichloride | Iomeprol |

The chemical formulae for these iodized contrast agents are as follows:
| Name of contrast agent (active principle and associated commercial name) | Chemical formula |
|---|---|
| Iobitridol (XENETIX ®) | 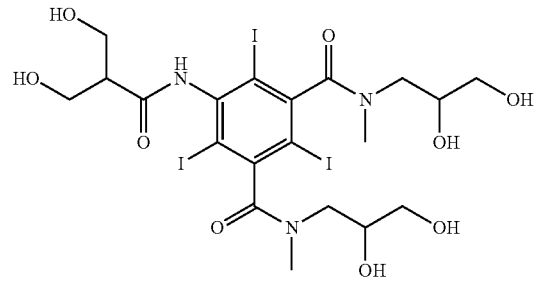 [SMILES: CN(CC(O)CO)C(=O)c1c(I)c(NC(=O)C(CO)CO)c(I)c(C(=O)N(C)CC(O)CO)c1I] |
| Iopamidol (IOPAMIRON ®) | 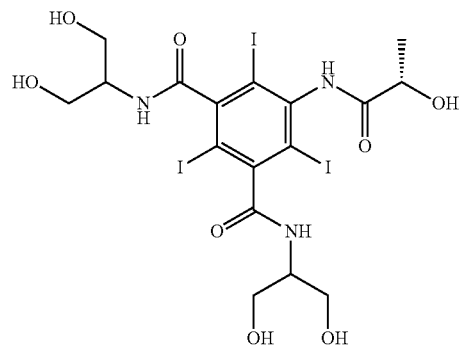 [SMILES: C[C@H](O)C(=O)Nc1c(I)c(C(=O)NC(CO)CO)c(I)c(C(=O)NC(CO)CO)c1I] |
| Iohexol (OMNIPAQUE ®) | 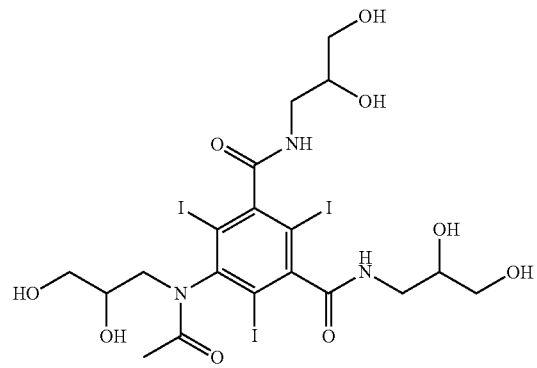 [SMILES: CC(=O)N(CC(O)CO)c1c(I)c(C(=O)NCC(O)CO)c(I)c(C(=O)NCC(O)CO)c1I] |
| Iodixanol (VISIPAQUE ®) | 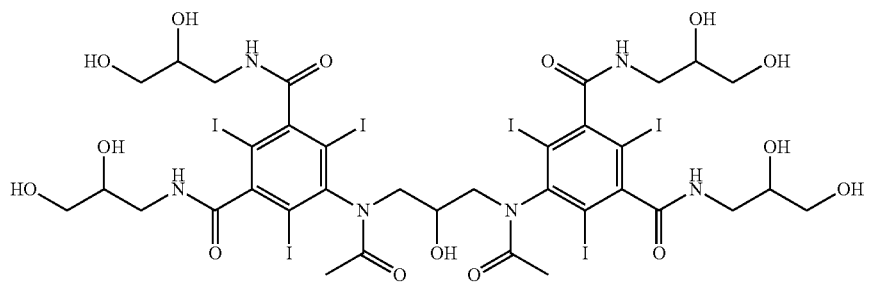 [SMILES: CC(=O)N(CC(O)CN(C(C)=O)c1c(I)c(C(=O)NCC(O)CO)c(I)c(C(=O)NCC(O)CO)c1I)c1c(I)c(C(=O)NCC(O)CO)c(I)c(C(=O)NCC(O)CO)c1I] |

| Name of contrast agent (active principle and associated commercial name | Chemical formula |
|---|---|
| Ioversol (OPTIJECT®) | 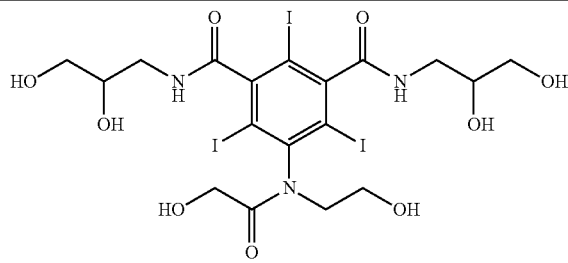 |
| Iomeprol (IOMERON®) | 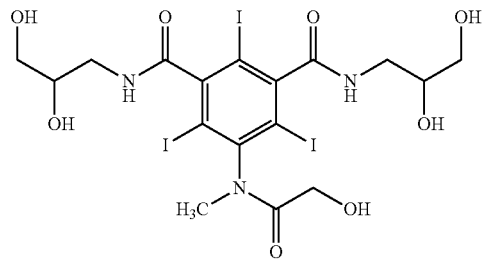 [SMILES: CN(C(=O)CO)c1c(I)c(C(=O)NCC(O)CO)c(I)c(C(=O)NCC(O)CO)c1I] |

In accordance with one embodiment, the organo-iodized compounds obtained, preferably with general formula (I) in accordance with the invention, can be used as intermediates in the synthesis of the following contrast agents: Iobitridol, Iopamidol, Iohexol, Iodixanol, Iomeprol and Ioversol.

In accordance with one embodiment, the steps a) and b) are carried out in the presence of an aprotic and polar solvent.

In accordance with one embodiment, the steps a) and b) are carried out in the presence of at least one solvent selected from the group constituted by dimethylacetamide, propylene carbonate, acetonitrile and tetrahydrofuran or a mixture thereof. Preferably, the solvent comprises a mixture of dimethylacetamide and propylene carbonate.

Because steps a) and b) are carried out in a one-pot setup, step b) is carried out in the reaction medium resulting from step a): the solvent(s) used as well as their quantity(ies) are thus preferably identical. In accordance with one embodiment, during step b), one or more solvent(s) may be added to that(those) used for step a).

In accordance with another embodiment, the ratio, in litres per kilogram, between the quantity of solvent (in litres) and the quantity of 2,4,6-triiodo-5-aminoisophthalic acid (in kg) is in the range 5 to 1 to 1 to 1, preferably in the range 3 to 1 to 2.5 to 1.

Step a) for Acylation

In accordance with one embodiment, the acylation of step a) is carried out in the presence of an acylation agent selected from DHP-COCl, acetyl chloride, 2-acetoxypropionyl chloride, chloroacetyl chloride, and acetoxyacetyl chloride.

These acylation agents have the following chemical formulae:

| Name of acylation agent | CAS number | Chemical formula |
|---|---|---|
| 2-(1-methylethyl)-1,3-dioxane-5-carboxylic acid chloride (DHPCOCl) | 116193-72-7 | |
| Ethanoyl chloride or acetyl chloride | 75-36-5 | |
| 2-acetoxypropionyl chloride (or (2S)-1-chloro-1-oxopropan-2-ylacetate) | 13831-31-7 | |
| Chloroacetyl chloride | 79-04-9 | |
| Acetoxyacetyl chloride | 13831-31-7 | |

In accordance with one embodiment, the acylation of step a) is carried out in the presence of an acylation agent, preferably an acyl chloride, present in a quantity in the range 1 to 1.5 molar equivalents with respect to the quantity of 2,4,6-triiodo-5-aminoisophthalic acid; preferably in the range 1.1 to 1.3, for example 1.1 or 1.3 molar equivalents with respect to the quantity of 2,4,6-triiodo-5-aminoisophthalic acid.

Step b) for Chlorination

In accordance with one embodiment, the chlorination of step b) is carried out in the presence of a chlorination agent selected from the group constituted by thionyl chloride, phosphorus oxychloride, phosphorus trichloride, oxalyl chloride, phosphorus pentachloride and methanoyl dichloride. In accordance with one embodiment, the chlorination of step b) is carried out in the presence of a reagent selected from the group constituted by thionyl chloride, phosphorus trichloride and phosphorus pentachloride. Preferably, the chlorination agent is thionyl chloride.

In accordance with one particular embodiment, the quantity of chlorination agent is in the range 2 to 6 molar equivalents with respect to the quantity of 2,4,6-triiodo-5-aminoisophthalic acid, preferably in the range 2.5 to 5 equivalents, more preferably in the range 3 to 5 equivalents, for example 3.5 or 5 equivalents, more preferably in the range 3.2 to 4 equivalents with respect to the quantity of 2,4,6-triiodo-5-aminoisophthalic acid.

Preparation of the Acylation Agent

In accordance with one embodiment, a step for the preparation of the acylation agent is carried out before step a), preferably without isolation of the acylation agent obtained. In accordance with one embodiment, the process comprises a one-pot concatenation of the following steps:
preparation of the acylation agent;
step a) for acylation, as defined above; and
step b) for chlorination, as defined above.

In particular, the synthesis of the acylation agent is carried out in the same reactor as that in which steps a) and b) in accordance with the invention will be carried out. Preferably, the acylation agent is prepared by chlorination of the carboxylic acid corresponding thereto. Preferably, the carboxylic acid corresponding to the acylation agent used in the preparation process in accordance with the invention is selected from 2-(1-methylethyl)-1,3-dioxane-5-carboxylic acid, acetic acid, acetoxypropionic acid, chloroacetic acid and acetoxyacetic acid.

In accordance with one embodiment, step a) is carried out for a period of 2 to 70 hours, preferably 2 to 24 h; and/or step b) is carried out for a period of 2 to 22 hours, preferably 4 to 12 h.

In accordance with another embodiment, step a) is carried out at a temperature of 10° C. to 70° C., preferably 15° C. to 60° C., more preferably 15° C. to 30° C., for example in the range 15° C. to 20° C. In accordance with another embodiment, step b) is carried out at a temperature of −15° C. to 30° C., preferably −10° C. to 10° C., yet more preferably 0° C. to 10° C.

Intermediate Compounds Y of the Preparation

The present invention also concerns a compound with the following general formula (Y1):

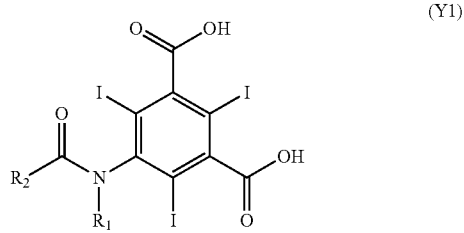

(Y1)

$R_1$ being H or a methyl group, $R_1$ preferably being H, and $R_2$ being selected from the group constituted by:
($C_1$-$C_{20}$)alkyl, linear or branched;
($C_1$-$C_{20}$)alkenyl, linear or branched;
($C_1$-$C_{20}$)alkynyl, linear or branched;
($C_3$-$C_{10}$)cycloalkyl;
($C_6$-$C_{10}$)aryl;
a heterocyclyl comprising 3 to 10 atoms; and
a heteroaryl comprising 6 to 10 atoms;

said alkyl, alkenyl and/or alkynyl groups optionally being substituted with one or more substituent(s) selected from the group constituted by atoms of halogen, oxygen and nitrogen;

said alkyl, alkenyl and/or alkynyl groups optionally being interrupted by one or more group(s) selected from the group constituted by —O—, —C(O)—O— and —O—C(O)—; and said cycloalkyl, heterocyclyl, aryl and/or heteroaryl groups optionally being substituted with one or more substituent(s) selected from the group constituted by ($C_1$-$C_{20}$)alkyl, which may be linear or branched, and atoms of halogen, oxygen and nitrogen;

with the condition that $R_2$ is different from the group

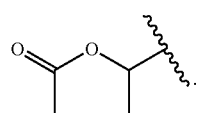 [SMILES: *C(C)OC(C)=O]

In accordance with one embodiment, $R_2$ is as defined above for the organo-iodized compounds with general formula (I), with the condition that $R_2$ is different from the group

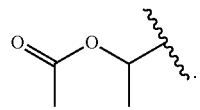

Preferably, the above compound has one of the following formulae:

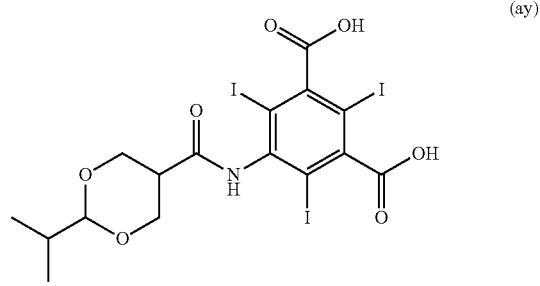 [SMILES: CC(C)C1OCC(C(=O)Nc2c(I)c(C(=O)O)c(I)c(C(=O)O)c2I)CO1]

(ay)

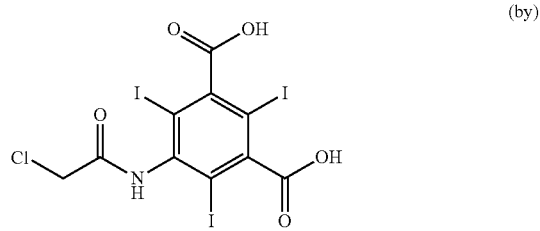

(by)

17

-continued

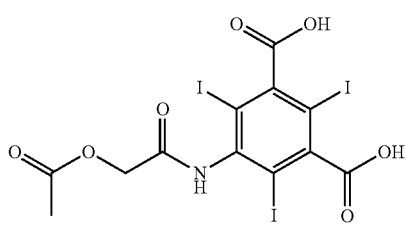
(cy)

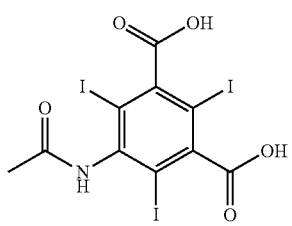
(dy)

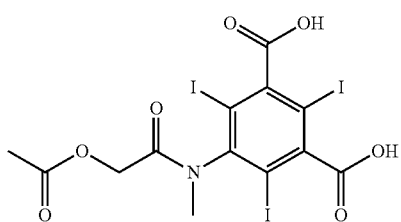
(ey)

Preferably, the compounds are the compounds (ay), (by) and (cy). The compounds with general formula (Y1) correspond in particular to the intermediate compounds Y as defined above.

The present invention also concerns the use of compounds with general formula (Y1) as defined above, for the preparation of organo-iodized compounds, preferably with general formula (I) as defined above.

The present invention also concerns the use of compounds with general formula (Y1) as defined above for the preparation of contrast agents, preferably for the preparation of iodized contrast agents and yet more preferably for the preparation of iopamidol (Iopamiron®), iohexol (Omnipaque®), ioversol (Optiray®), iomeprol (Iomeron®) or iobitridol (Xenetix®).

Preferably, the present invention concerns the use of the compound with general formula:

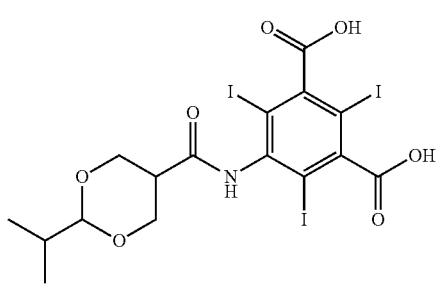
(ay)

18 for the preparation of iobitridol, and/or the use of the compound with general formula

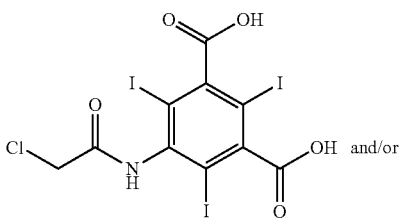
(by)

and/or

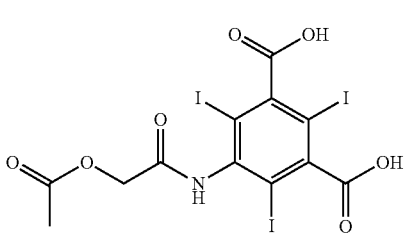
(cy)

for the preparation of ioversol, and/or the use of the compound with general formula (ey) for the preparation of iomeprol.

The examples given below are presented by way of illustration and are not a limitation of the invention.

EXAMPLES

Analytical Methods Used

The synthesis compounds were analysed using two Nuclear Magnetic Resonance techniques: proton NMR at 400 MHz and carbon-13 NMR at 100 MHz. The compounds were dissolved in DMSO-d6. The compounds were also analysed by Mass Spectrometry, in negative mode and in positive mode. The NMR identification was carried out using a 400 MHz NMR spectrometer from Bruker. The MS identification was carried out using a Thermo Fischer Q-Exactive Orbitrap type mass spectrometer.

The term "V" is intended to designate a volume ratio, i.e. the volume of a reagent or a solvent with respect to 1 kg of AATI.

The term "eq" is intended to designate a number for a molar equivalent, i.e. the ratio between the number of moles of a reagent and the number of moles of AATI.

Example 1: Synthesis of 5-[[[2-(1-methylethyl)-1,3-dioxan-5-yl]carbonyl]amino-2,4,6-triiodo-1,3-benzenedicarbonyl dichloride (DICOA)

General scheme for the synthesis

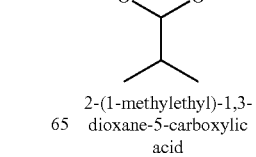

2-(1-methylethyl)-1,3-dioxane-5-carboxylic acid

→

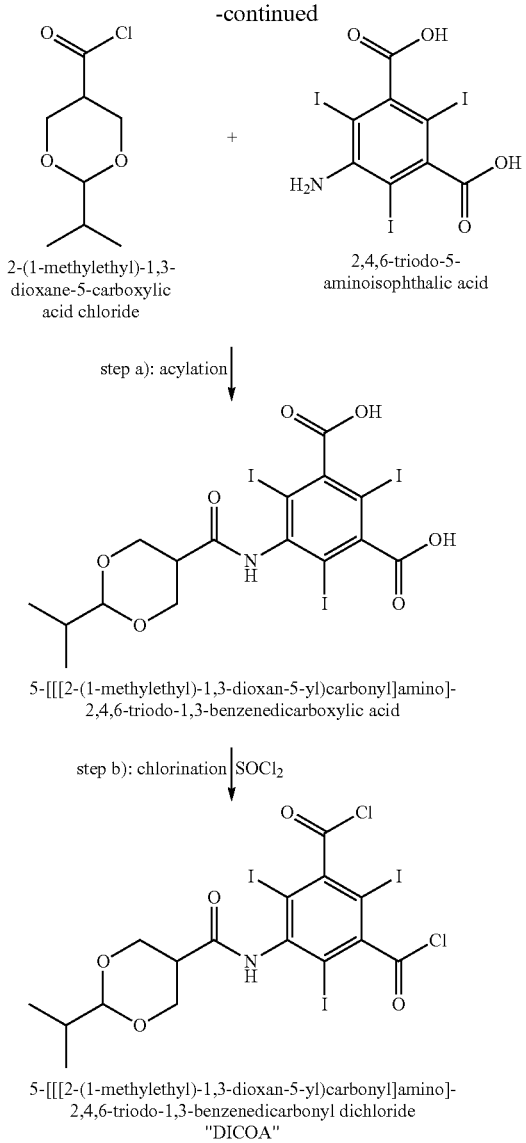

2-(1-methylethyl)-1,3-dioxane-5-carboxylic acid chloride 2,4,6-triodo-5-aminoisophthalic acid step a): acylation 5-[[[2-(1-methylethyl)-1,3-dioxan-5-yl)carbonyl]amino]-2,4,6-triodo-1,3-benzenedicarboxylic acid step b): chlorination | SOCl₂

5-[[[2-(1-methylethyl)-1,3-dioxan-5-yl)carbonyl]amino]-2,4,6-triodo-1,3-benzenedicarbonyl dichloride
"DICOA"

Operating Method 1:
Acylation Step:

Dimethylacetamide (33.7 mL; 1.35 V) and 2-(1-methylethyl)-1,3-dioxane-5-carboxylic acid (8.7 g, 1.125 eq) were mixed at 25° C. until the starting acid had dissolved. The reaction medium was cooled to 0° C., then thionyl chloride (6.31 g, 1.06 eq/starting acid) was added over 1 h-1 h 30 between 0° C. and 15° C. The medium was stirred for 3 h at 15° C. in order to complete the reaction. Propylene carbonate (3.7 mL, 0.15 V) was added to a 250 mL reactor at 15° C.

Next, 5-amino-2,4,6-triiodoisophthalic acid (25 g; 1 eq) was introduced over 30 minutes. When introduction was complete, the medium was heated up to a temperature of 18° C., then the acylation reaction was carried out over a period of 24 hours at a temperature in the range 18° C. to 30° C.

The intermediate 5-[[[2-(1-methylethyl)-1,3-dioxan-5-yl]carbonyl]amino]-2,4,6-triiodo-1,3-benzenedicarboxylic acid (compound (ay)) was then formed.

The medium was then fluidified with propylene carbonate (25 mL; volume ratio of 1), then cooled to a temperature of 5° C.

Chlorination Step:

As soon as the medium had reached a temperature of 5° C., thionyl chloride (18 g; equivalent molar ratio of 3.5) was added. The thionyl chloride addition lasted 2 hours at a temperature of 5° C. When introduction of the reagent was complete, the chlorination reaction was carried out over a period of 5 hours at a temperature of 5° C.

The degree of conversion thus obtained was 85% (s/s) of 5-[[[2-(1-methylethyl)-1,3-dioxan-5-yl]carbonyl]amino]-2,4,6-triiodo-1,3 benzenedicarbonyl dichloride.

The reaction medium was slowly added to a mixture of water/ethanol/sodium acetate. The solid obtained was filtered, washed, dried then analysed.

The yield obtained was 82%.
Analytical Results:
Nuclear Magnetic Resonance:

$^1$H NMR (400 MHz, DMSO-d6) δ: 10.4 (s, 1H), 4.3 (d, J=4.9 Hz, 1H), 4.3 (m, 2H), 3.9 (t, J=11.4 Hz, 2H), 3.0 (ddt, J=11.1, 6.9, 4.6 Hz, 1H), 1.7 (dhept, J=6.9, 4.8 Hz, 1H), 0.9 (d, J=6.8 Hz, 6H).

$^{13}$C NMR (101 MHz, DMSO-d6) δ: 169.4-169.8, 168.3, 149.7-150.3, 143.1-143.9, 105.0, 87.1-102.0, 69.0, 41.9, 32.5, 17.3.

Mass Spectrometry:
[M−H]⁻=749.7321 uma (exact mass=749.7310 uma)
[M+H]⁺=751.7453 uma (exact mass=751.7456 uma)

Operating Method 2:
Acylation Step:

Dimethylacetamide (40 mL; 1.6 V) and 2-(1-methylethyl)-1,3-dioxane-5-carboxylic acid (10.2 g, 1.3 eq) were introduced into a reactor with a volume of 250 mL. The reaction medium was cooled to 0° C., then thionyl chloride (5.4 g 1.06 eq/starting acid) was added over 1 h-1 h 30 at between 0° C. and 15° C. The medium was stirred for 3 h at 15° C. in order to complete the reaction. Next, 5-amino-2,4,6-triiodoisophthalic acid (25 g, 1 eq) was introduced over 30 minutes.

When introduction was complete, the medium was heated up to a temperature of 18° C., then the acylation reaction was carried out over a period of 70 hours at a temperature of 18° C.

The intermediate 5-[[[2-(1-methylethyl)-1,3-dioxan-5-yl]carbonyl]amino]-2,4,6-triiodo-1,3-benzenedicarboxylic acid (compound (ay)) was then formed.

Chlorination Step:

The reaction medium was then cooled to a temperature of −10° C. As soon as the medium had reached a temperature of −10° C., thionyl chloride (26.6 g, 5 eq) was added. The thionyl chloride addition lasted 2 hours, at a temperature of −10° C. When introduction of the reagent was complete, the chlorination reaction was carried out over a period of 12 hours at a temperature of −10° C.

The degree of conversion thus obtained was 86% (s/s) of 5-[[[2-(1-methylethyl)-1,3-dioxan-5-yl]carbonyl]amino]-2,4,6-triiodo-1,3-benzenedicarbonyl dichloride.

The reaction medium was then slowly added to a mixture of water/ethanol/sodium acetate. The solid obtained was filtered, washed, dried then analysed.

The yield obtained was 84.5%
Analytical Results:
Nuclear Magnetic Resonance:

$^1$H NMR (400 MHz, DMSO-d6) δ: 10.4 (s, 1H), 4.3 (d, J=4.9 Hz, 1H), 4.3 (m, 2H), 3.9 (t, J=11.4 Hz, 2H), 3.0 (ddt, J=11.1, 6.9, 4.6 Hz, 1H), 1.7 (dhept, J=6.9, 4.8 Hz, 1H), 0.9 (d, J=6.8 Hz, 6H), $^{13}$C NMR (101 MHz, DMSO-d6) δ: 169.4-169.8, 168.3, 149.7-150.3, 143.1-143.9, 105.0, 87.1-102.0, 69.0, 41.9, 32.5, 17.3.

Mass Spectrometry:

[M−H]$^-$=749.7321 uma (exact mass=749.7310 uma)
[M+H]$^+$=751.7453 uma (exact mass=751.7456 uma)

Example 2: Synthesis of 5-(acetylamino)-2,4,6-triiodobenzene-1,3-dicarbonyl dichloride (Intermediate in the Synthesis of Iohexol/Iodixanol)

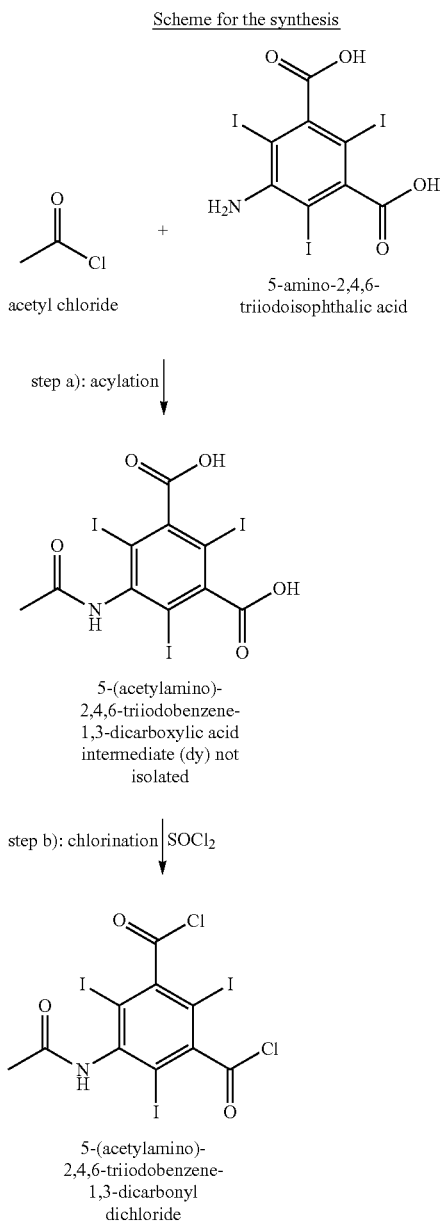

Acylation Step:

Dimethylacetamide (67.5 mL; 1.35 V) and propylene carbonate (7.5 mL; 0.15 V) were mixed in a reactor with a volume of 250 mL.

Acetyl chloride (7.7 g; 1.1 eq) was then added to the mixture. After cooling to a temperature of 15° C., 5-amino-2,4,6-triiodoisophthalic acid (50 g; 1 eq) was introduced over 30 minutes. When introduction was complete, the medium was heated up to a temperature of 18° C., then the acylation reaction was carried out over a period of 36 hours at a temperature of 18° C.

The intermediate 5-(acetylamino)-2,4,6-thiodobenzene-1,3-dicarboxylic acid (compound (dy)) was then formed.

The medium was then fluidified with dimethylacetamide (50 mL; 1 V) and propylene carbonate (50 mL; 1 V). Next, the medium was cooled to a temperature of 5° C.

Chlorination Step:

As soon as the medium had reached a temperature of 5° C., thionyl chloride (52.8 g; 5 eq) was added. The thionyl chloride addition lasted 2 hours at a temperature of 5° C. When introduction of the reagent was complete, the chlorination reaction was carried out over a period of 5 hours at a temperature of 5° C.

The degree of conversion thus obtained was 85% (s/s) of 5-(acetylamino)-2,4,6-triiodobenzene-1,3-dicarbonyl dichloride.

The reaction medium was slowly added to a mixture of water/ethanol/sodium acetate. The solid obtained was filtered, washed, dried then analysed.

The yield obtained was 60%.

Analytical Results:

Nuclear Magnetic Resonance:

$^1$H NMR (400 MHz, DMSO-d6) δ: 10.1 (s, 1H), 2.1 (s, 3H).

$^{13}$C NMR (101 MHz, DMSO-d6) δ: 168.3, 144.1-150.2, 86.8-102.2, 169.5-169.8, 144.8, 23.4.

Mass Spectrometry:

[M−H]$^-$=635.6634 uma (exact mass=635.6630 uma)
[M+Na]$^+$=659.6593 uma (exact mass=659.6594 uma)

Example 3: Synthesis of 5-{[(2S)-2-(acetyloxy)-1-oxopropyl}amino-2,4,6-triiodo-1,3-benzenedicarbonyl dichloride (Intermediate in the Synthesis of Iopamidol)

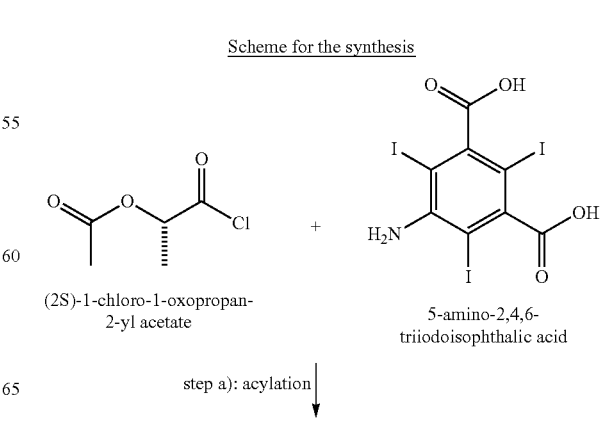

step a): acylation

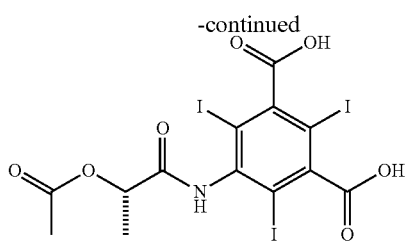

5-{[(2S)-2-(acetyloxy)-1-oxopropyl]amino}-2,4,6-triiodo-1,3-benzenedicarboxylic acid intermediate (ey) not isolated step b): chlorination | SOCl$_2$

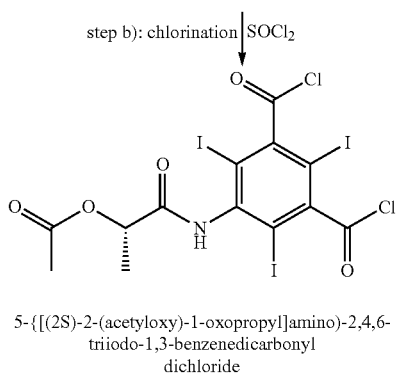

5-{[(2S)-2-(acetyloxy)-1-oxopropyl]amino}-2,4,6-triiodo-1,3-benzenedicarbonyl dichloride Acylation Step:

Dimethylacetamide (34 mL; 1.35 V) and propylene carbonate (3.75 mL; 0.15 V) were mixed in a reactor with a volume of 250 mL.

(2S)-1-chloro-1-oxopropan-2-yl acetate (7.5 g; 1.1 eq) was then added to the mixture. After cooling to a temperature of 15° C., 5-amino-2,4,6-triiodoisophthalic acid (25 grams; 1 eq) was introduced over 30 minutes. When introduction was complete, the medium was heated up to a temperature of 18° C., then the acylation reaction was carried out over a period of 66 hours at a temperature of 18° C.

The intermediate 5-{[(2S)-2-(acetyloxy)-1-oxopropyl}amino-2,4,6-triiodo-1,3-benzenedicarboxylic acid (compound (ey)) was then formed.

The medium was then diluted with propylene carbonate (25 mL, 1 V). Next, the medium was cooled to a temperature of 5° C.

Chlorination Step:

As soon as the medium had reached a temperature of 5° C., thionyl chloride (18.5 g; 3.5 eq) was added. The thionyl chloride addition lasted 1 hour at a temperature of 5° C. When introduction of the reagent was complete, the chlorination reaction was carried out over a period of 5 hours at a temperature of 5° C.

The degree of conversion thus obtained was 87% (s/s) of 5-{[(2S)-2-(acetyloxy)-1-oxopropyl}amino-2,4,6-triiodo-1,3-benzendicarbonyl dichloride.

The reaction medium was slowly added to a mixture of water/ethanol/sodium acetate. The solid obtained was filtered, washed, dried then analysed.

The yield obtained was 70%.

Analytical Results:

Nuclear Magnetic Resonance:

$^1$H NMR (400 MHz, DMSO-d6) δ: 10.3 (s, 1H), 5.2 (q, J=6.9 Hz, 1H), 2.1 (s, 3H), 1.5 (d, J=6.9 Hz, 3H).

$^{13}$C NMR (101 MHz, DMSO-d6) δ: 142.9-150.4, 87.2-101.9, 168.5-170.0, 169.9, 168.9, 69.9, 21.3, 18.0.

Mass Spectrometry:

[M−H]$^−$=707.6847 uma (exact mass=707.6841 uma)
[M+Na]$^+$=731.6806 uma (exact mass=731.6806 uma)

Example 4: Synthesis of 5-{[(acetyloxy)acetyl]amino}-2,4,6-triiodobenzene-1,3-dicarbonyl dichloride (Intermediate in the Synthesis of Ioversol)

Scheme for the synthesis

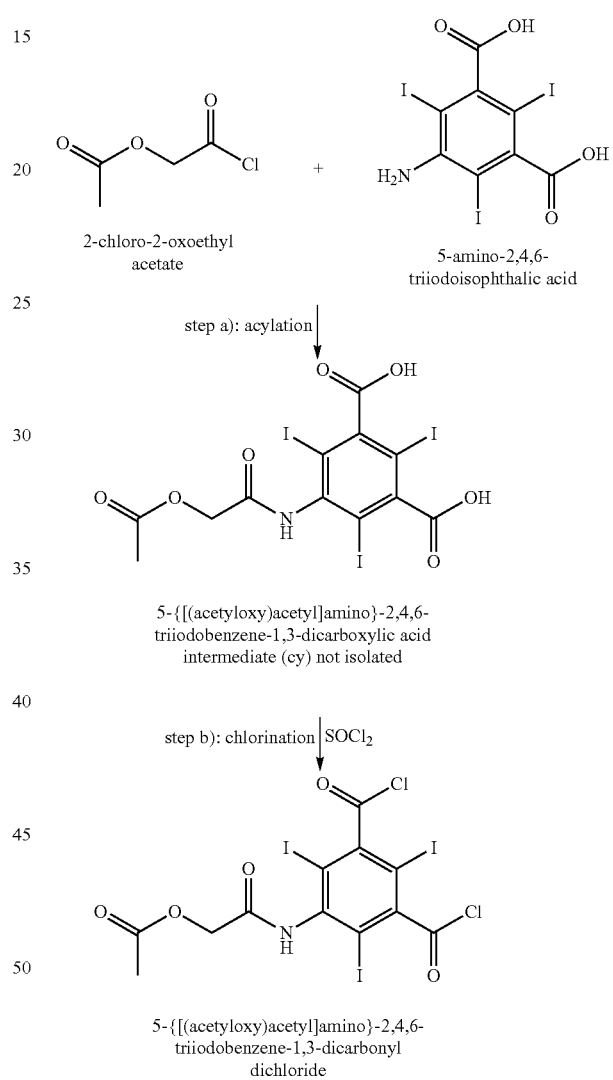

Acylation Step:

Dimethylacetamide (67.5 mL, 1.35 V) and propylene carbonate (7.5 mL; 0.15 V) were mixed in a reactor with a volume of 250 mL.

2-chloro-2-oxoethyl acetate (13.3 g; 1.1 eq) was then added to the mixture. After cooling to a temperature of 15° C., 5-amino-2,4,6-triiodoisophthalic acid (50 g; 1 eq) was introduced over 45 minutes. When introduction was complete, the medium was heated up to a temperature of 18° C., then the acylation reaction was carried out over a period of 65 hours at a temperature of 18° C.

The intermediate 5-{[(acetyloxy)acetyl]amino}-2,4,6-triiodobenzene-1,3-dicarboxylic acid (compound (cy)) was then formed.

The medium was then diluted with propylene carbonate (50 mL; 1 V). Next, the medium was cooled to a temperature of 5° C.

Chlorination Step:

As soon as the medium had reached a temperature of 5° C., thionyl chloride (37 g; 3.5 eq) was added. The thionyl chloride addition lasted 2 hours at a temperature of 5° C. When introduction of the reagent was complete, the chlorination reaction was carried out over a period of 4 hours at a temperature of 5° C.

The degree of conversion thus obtained was 90.5% (s/s) of 5-{[(acetyloxy)acetyl]amino}-2,4,6-triiodobenzene-1,3-dicarbonyl dichloride.

The reaction medium was slowly added to a mixture of water/ethanol/sodium acetate. The solid obtained was filtered, washed, dried then analysed. The yield obtained was 87%.

Analytical Results:

Nuclear Magnetic Resonance:

$^1$H NMR (400 MHz, DMSO-d6) δ: 10.4 (s, 1H), 4.7 (s, 2H), 2.2 (s, 3H).

$^{13}$C NMR (101 MHz, DMSO-d6) δ: 143.0-150.3, 87.3-102.0, 169.4-169.8, 170.1, 166.1, 62.6, 21.0.

Mass Spectrometry:

[M−H]$^−$=693.6691 uma (exact mass=693.6684 uma)
[M+Na]$^+$=717.6645 uma (exact mass=717.6649 uma)

Example 5: Synthesis of 5-[(chloroacetyl)amino]-2,4,6-triiodobenzene-1,3-dicarbonyl dichloride (Intermediate in the Synthesis of Ioversol)

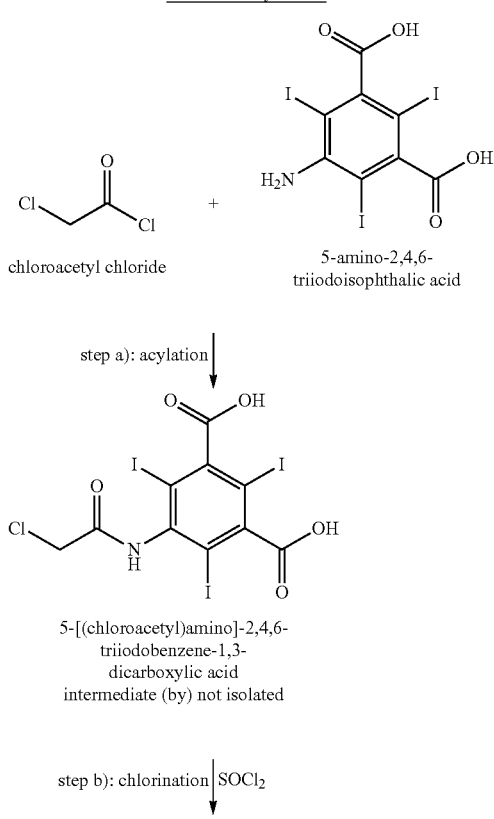

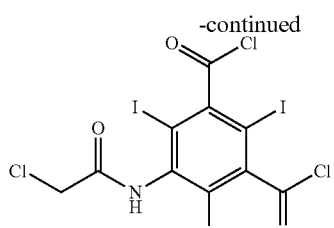

5-[(chloroacetyl)amino]-2,4,6-triiodobenzene-1,3-dicarbonyl dichloride

Acylation Step:

Dimethylacetamide (67.5 mL; 1.35 V) and propylene carbonate (7.5 mL; 0.15 V) were mixed in a reactor with a volume of 250 mL.

Chloroacetyl chloride (11 g; 1.1 eq) was then added to the mixture. After cooling to a temperature of 15° C., 5-amino-2,4,6-triiodoisophthalic acid (50 g; 1 eq), was introduced in portions, i.e. approximately 3.4 g every two minutes, over 30 minutes. When introduction was complete, the medium was heated up to a temperature of 18° C., then the acylation reaction was carried out over a period of 40 hours at a temperature of 18° C.

The intermediate 5-[(chloroacetyl)amino]-2,4,6-triiodobenzene-1,3-dicarboxylic acid (compound (by)) was then formed.

The medium was then fluidified with dimethylacetamide (50 mL; 1 V) and propylene carbonate (50 mL; 1 V). Next, the medium was cooled to a temperature of 5° C.

Chlorination Step:

As soon as the medium had reached a temperature of 5° C., thionyl chloride (52.9 g; 5 eq) was added. The thionyl chloride addition lasted 3 hours at a temperature of 5° C. When introduction of the reagent was complete, the chlorination reaction was carried out over a period of 18 hours at a temperature of 5° C.

The degree of conversion thus obtained was 88% (s/s) of 5-[(chloroacetyl)amino]-2,4,6-triiodobenzene-1,3-dicarbonyl dichloride.

The reaction medium was slowly added to a mixture of water/ethanol/sodium acetate. The solid obtained was filtered, washed, dried then analysed. The yield obtained was 86%.

Analytical Results:

Nuclear Magnetic Resonance $^1$H NMR (400 MHz, DMSO-d6) δ: 10.6 (s, 1H), 4.4 (s, 2H).

$^{13}$C NMR (101 MHz, DMSO-d6) δ: 142.9-150.3, 87.5-101.8, 169.4-169.8, 164.8, 98.4, 43.3.

Mass Spectrometry:

[M−H]$^−$=669.6245 uma (exact mass=669.6240 uma)
[M+Na]$^+$=693.6202 uma (exact mass=693.6205 uma)

The invention claimed is:

1. A compound having a chemical structure corresponding to formula (Y1):

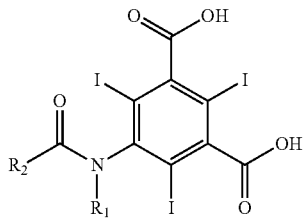
(Y1)

wherein:
R₁ is a methyl group; and
R₂ is selected from the group consisting of:
  $(C_1-C_{20})$alkyl, linear or branched;
  $(C_1-C_{20})$alkenyl, linear or branched;
  $(C_1-C_{20})$alkynyl, linear or branched;
  $(C_3-C_{10})$cycloalkyl;
  $(C_6-C_{10})$aryl;
  a heterocyclyl comprising 3 to 10 atoms; and
  a heteroaryl comprising 6 to 10 atoms;
wherein:
  said alkyl, alkenyl and/or alkynyl groups optionally being substituted with one or more substituent(s) selected from the group consisting of halogen, oxygen and nitrogen;
  said alkyl, alkenyl and/or alkynyl groups optionally being interrupted by one or more group(s) selected from the group consisting of —O—, C(O)—O— and —O—C(O)—; and
  said cycloalkyl, heterocyclyl, aryl and/or heteroaryl groups optionally being substituted with one or more substituent(s) selected from the group consisting of $(C_1-C_{20})$alkyl, which may be linear or branched, halogen, oxygen and nitrogen; and
wherein R₂ is not

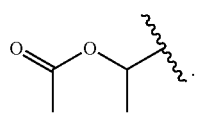

2. A compound having a chemical structure corresponding to formula (ay), formula (cy), or formula (ey) as depicted below:

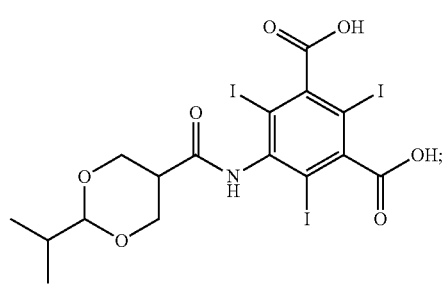
(ay)

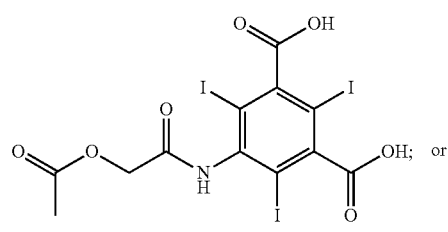
(cy)

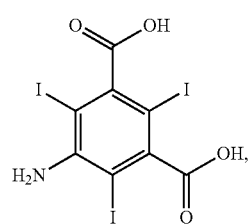
(ey)

3. A process for preparing an organo-iodized compound, the process comprising the following steps:
a) acylating 2,4,6-triiodo-5-aminoisophthalic acid having a chemical structure corresponding to formula (A):

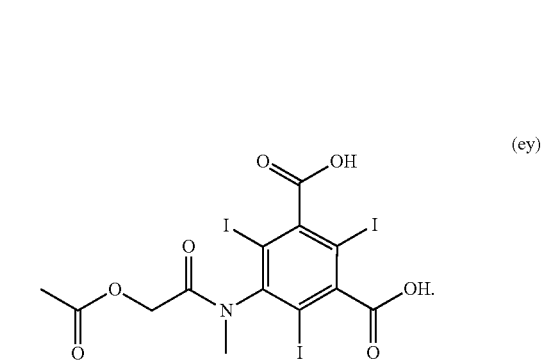
(A)

or 2,4,6-triiodo-N-methyl-5-aminoisophthalic acid having the following chemical structure:

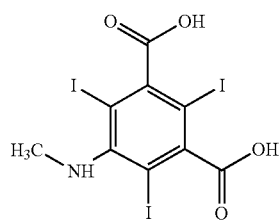

with a compound having a chemical structure corresponding to formula (II):

R₂—C(O)Cl    (II)

to form an intermediate compound having a chemical structure corresponding to formula (Y1):

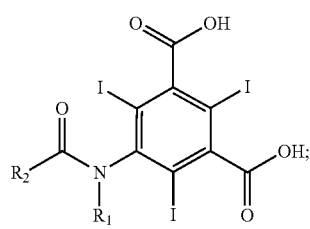

(Y1)

b) chlorinating the intermediate compound Y1 in the presence of a chorination agent, wherein chlorination agent is at an amount in a range 2 to 6 molar equivalents relative to the amount of the 2,4,6-triiodo-5-aminoisophthalic acid or 2,4,6-triiodo-N-methyl-5-aminoisophthalic acid, to form the organo-iodized compound, which has a chemical structure corresponding to formula (I):

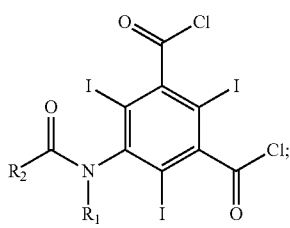

(I)

wherein:

$R_1$ is H or a methyl group; and $R_2$ is selected from the group consisting of:
  $(C_1-C_{20})$alkyl, linear or branched;
  $(C_1-C_{20})$alkenyl, linear or branched;
  $(C_1-C_{20})$alkynyl, linear or branched;
  $(C_3-C_{10})$cycloalkyl; $(C_6-C_{10})$aryl;
  a heterocyclyl comprising 3 to 10 atoms; and
  a heteroaryl comprising 6 to 10 atoms;

wherein:
  said alkyl, alkenyl and/or alkynyl groups optionally being substituted with one or more substituent(s) that comprise(s) one or more atoms selected from the group consisting of halogen, oxygen and nitrogen;
  said alkyl, alkenyl and/or alkynyl groups optionally being interrupted by one or more group(s) selected from the group consisting of —O—, —C(O)—O— and —O—C(O)—; and
  said cycloalkyl, heterocyclyl, aryl and/or heteroaryl groups optionally being substituted with one or more substituent(s) that is/are $(C_1-C_{20})$alkyl, which may be linear or branched, or that comprise(s) one or more atoms selected from the group consisting of halogen, oxygen and nitrogen;

wherein the steps a) and b) are performed without isolating the intermediate compound Y1.

4. The process of claim 3, wherein the steps a) and b) are carried out in a single reactor.

5. The process of claim 3, wherein $R_2$ is selected from the group consisting of:

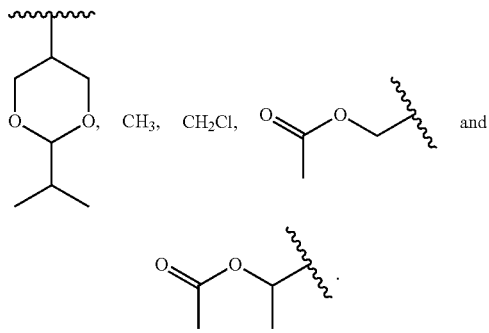

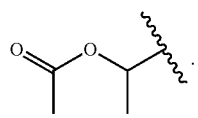

6. The process of claim 3, wherein steps a) and b) are carried out in the presence of a solvent selected from the group consisting of dimethylacetamide, propylene carbonate, acetonitrile, tetrahydrofuran, and mixtures thereof.

7. The process of claim 3, wherein step b) is carried out in the presence of a chlorination agent selected from the group consisting of thionyl chloride, phosphorus oxychloride, phosphorus trichloride, oxalyl chloride, phosphorus pentachloride, and methanoyl dichloride.

8. The process of claim 3, wherein $R_2$ is not

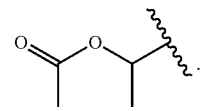

9. The process of claim 3, wherein the intermediate compound (Y1) has a chemical structure corresponding to formula (ay), formula (cy), or formula (ey) as depicted below:

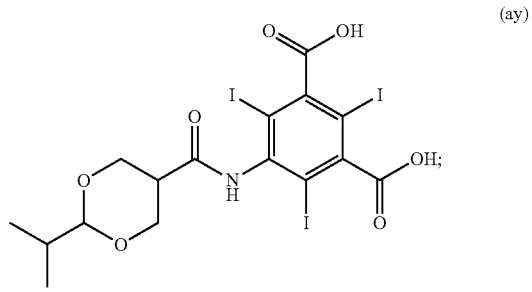

(ay)

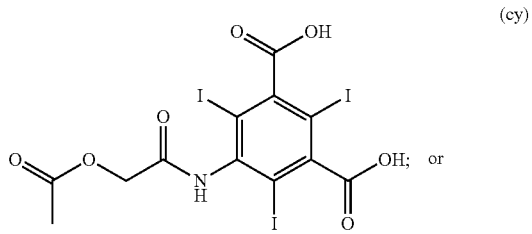

(cy)

or

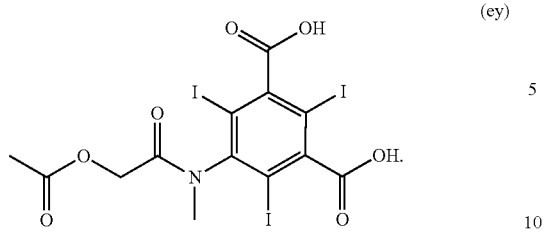
10. The process of claim 3, wherein step a) is the acylation of 2,4,6-triiodo-5-aminoisophthalic acid having a chemical structure corresponding to formula (A) with a compound having a chemical structure corresponding to formula (II), and wherein $R_1$ is H.
* * * * *